United States Patent

Buschmann et al.

[11] Patent Number: 4,895,586
[45] Date of Patent: Jan. 23, 1990

[54] TRIAZOLYL GLYCOL ETHERS, FUNGICIDES AND BIOREGULATORS

[75] Inventors: Ernst Buschmann, Ludwigshafen; Linhard Sproesser, Bad Duerkheim; Bernd Zeeh, Limburgerhof; Johann Jung, Limburgerhof; Wilhelm Rademacher, Limburgerhof; Ernst-Heinrich Pommer, Limburgerhof; Eberhard Ammermann, Ludwigshafen, all of Fed. Rep. of Germany

[73] Assignee: BASF Aktiengesellschaft, Ludwigshafen, Fed. Rep. of Germany

[21] Appl. No.: 932,338

[22] Filed: Nov. 19, 1986

[30] Foreign Application Priority Data

Nov. 21, 1985 [DE] Fed. Rep. of Germany ....... 3541156

[51] Int. Cl.$^4$ ................ A01N 43/653; C07D 249/08
[52] U.S. Cl. ........................................... 71/76; 71/92; 514/383; 548/262
[58] Field of Search .................. 548/262; 514/383; 71/76, 92

[56] References Cited

U.S. PATENT DOCUMENTS 4,319,911 3/1982 Ammermann et al. ............. 548/262
4,411,687 10/1983 Zieh et al. ............................ 548/262

FOREIGN PATENT DOCUMENTS 0092674 3/1983 European Pat. Off. ............ 548/262

Primary Examiner—Richard L. Raymond
Assistant Examiner—Patricia L. Morris
Attorney, Agent, or Firm—Keil & Weinkauf

[57] ABSTRACT

α-triazolyl glycol ethers of the formula I

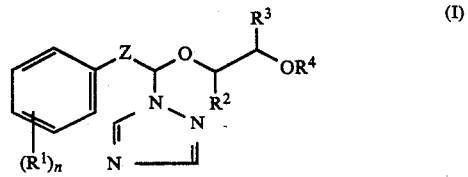

where
$R^1$ is alkyl, alkoxy, halogen or phenyl,
$R^2$ and $R^3$ are each hydrogen or alkyl,
$R^4$ is alkyl or unsubstituted or substituted phenyl,
Z is

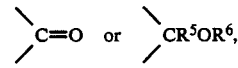

n is 0, 1, 2 or 3,
$R^5$ is hydrogen, alkyl, alkenyl or alkynyl and
$R^6$ is hydrogen, alkyl, alkenyl or unsubstituted or substituted benzyl,
a process for their preparation, and their use as crop protection agents and growth regulators.

5 Claims, No Drawings

TRIAZOLYL GLYCOL ETHERS, FUNGICIDES AND BIOREGULATORS

The present invention relates to novel triazolyl glycol ethers, fungicides and/or plant growth regulators which contain these triazolyl glycol ethers, and the use of these compounds or fungicides or plant growth regulators for controlling fungi or for regulating plant growth.

German Laid-Open Application DOS 3,047,726 discloses the use of certain triazolyl ethers as bioregulators. However, the plant growth-regulating action of these substances, their degradability in the soil, their species-specific applicability and their toleration by crops do not meet all requirements.

We have found that triazolyl glycol ethers I

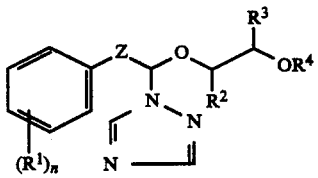

where
$R^1$ is alkyl, alkoxy, halogen or phenyl,
$R^2$ and $R^3$ are each hydrogen or alkyl,
$R^4$ is alkyl or unsubstituted or substituted phenyl,
Z is

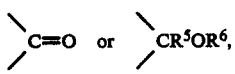

n is 0, 1, 2 or 3,
$R^5$ is hydrogen, alkyl alkenyl or alkynyl and
$R^6$ is hydrogen, alkyl, alkenyl or unsubstituted or substituted benzyl, have a good plant growth-regulating action which is superior to the action of known triazolyl ethers and moreover have a fungicidal action.

In the formula I, $R^1$ is preferably alkyl, such as methyl, ethyl, n-propyl, isopropyl, n-butyl, tert-butyl or isobutyl, a corresponding alkoxy radical of 1 to 4 carbon atoms, fluorine, bromine, chlorine, iodine or phenyl.

$R^2$ and $R^3$ independently of one another are each hydrogen or alkyl of 1 to 4 carbon atoms, ie. methyl, ethyl, n-propyl, isopropyl, n-butyl, tert-butyl or isobutyl.

$R^4$ is preferably alkyl, such as methyl, ethyl, n-propyl, isopropyl, n-butyl, tert-butyl or isobutyl, phenyl or substituted phenyl, such as halophenyl (4-chlorophenyl, 2-chlorophenyl, 2,4-dichlorophenyl, 4-fluorophenyl or 4-bromophenyl), alkylphenyl (4-methylphenyl or 4-tert-butylphenyl) or alkoxy phenyl (4-methoxyphenyl, 2-methoxyphenyl or 4-isopropoxyphenyl).

$R^5$ is preferably hydrogen or alkyl, such as methyl, ethyl, n-propyl, isopropyl, n-butyl or isobutyl, alkenyl, such as vinyl, allyl or prop-1-en-1-yl, or alkynyl, such as ethynyl, prop-1-yn-1-yl or but-1-yn-1-yl.

$R^6$ is preferably alkyl, such as methyl, ethyl, n-propyl, isopropyl, n-butyl or isobutyl, alkenyl, such as allyl or crotyl, benzyl, or substituted benzyl, eg. halobenzyl (4-chlorobenzyl, 2-chlorobenzyl, 2,4-dichlorobenzyl or 4-fluorobenzyl), alkylbenzyl (4-methylbenzyl or 4-tert-butylbenzyl) or alkoxybenzyl (4-methoxybenzyl, 2-methoxybenzyl or 4-isopropoxybenzyl).

The triazolyl glycol ethers possess one or more centers of asymmetry and accordingly form different diastereomers or enantiomers, which can be isolated in pure form by a conventional method of resolution. For the purposes of the present invention suitable agents are both the pure enantiomers or diastereomers and the mixtures usually obtained in the synthesis.

The triazolyl glycol ethers of the formula I can readily be prepared if an appropriate benzoyl formaldehyde acetal II

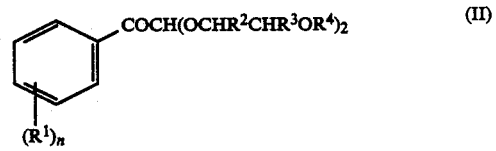

is reacted with acetyl bromide and 1,2,4-triazole to give a triazolyl ketone Ia

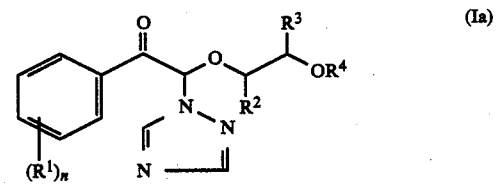

The ketone can be converted with a conventional agent to the corresponding carbinol Ib or Ic, and this can be converted to the corresponding ether Id or Ie.

The triazolyl ketone Ia can either be converted with a reducing agent, such as NaBH$_4$, LiAlH$_4$, or H$_2$/catalyst, to a triazolyl carbinol Ib

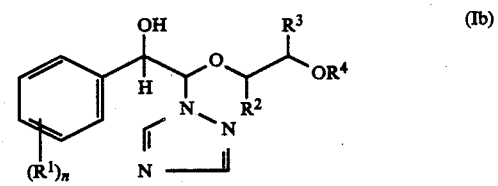

or be converted to a triazolyl carbinol Ic

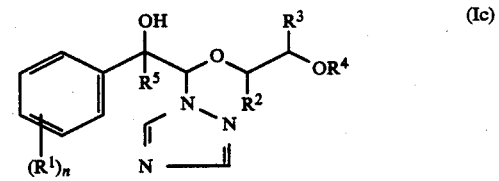

by a Grignard reaction or by means of an organolithium compound.

All these compounds are novel active ingredients, as are the ethers Id and Ie obtainable by esterifying the carbinols Ib and Ic.

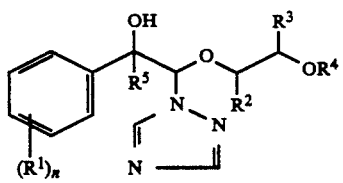

(Id ⟶ R⁵ = H ⟶ R⁶ ≠ H)

(Ie ⟶ R⁵ ≠ H ⟶ R⁶ ≠ H)

Some of the benzoylformaldehyde acetals of the formula (II) are disclosed in Japanese Preliminary Published Application J 57 210 076 (CA 96 (20): 164,204 c); in any case, the said benzoylformaldehyde acetals can be obtained by transacetalization of benzoylformaldehyde acetals which are known or which can be prepared in a conventional manner.

The preparation of the novel active ingredients is illustrated, by way of example, by the following reactions:

Stage A

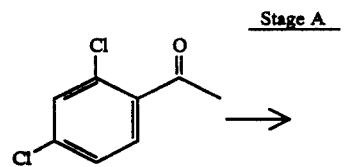

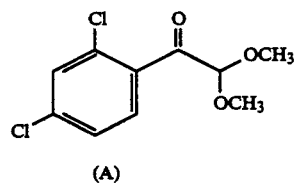

(A)

366 g of methyl nitrite gas are passed into a solution of 567 g of 2,4-dichloroacetophenone and 91 g of HCL in 2 l of methanol at room temperature. The mixture is stirred for a further 5 hours, neutralized with 30% strength sodium methylate and filtered under suction, the filtrate is taken up with methylene chloride, the solution is washed with water, dried over sodium sulfate and evaporated down and the residue is distilled to give 535 g of ω,ω-dimethoxy-2,4-dichloroacetophenone (A) of boiling point 132°–136° C./0.7 mbar.

Stage B

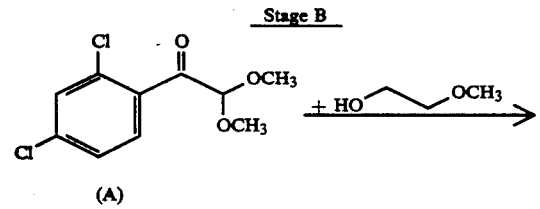

(A)

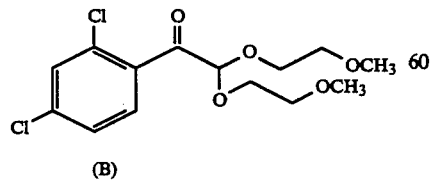

(B)

A solution of 100 g of (A) and 10 g of HCl in 230 g of ethylene glycol monomethyl ether is stirred for 15 hours at room temperature and then evaporated down slowly under reduced pressure from a water pump. If conversion is found to be incomplete (GC check), further ethylene glycol monomethyl ether and HCl are added and the mixture is evaporated down again. The crude product is taken up with methylene chloride, and the solution is washed with aqueous sodium bicarbonate solution, dried over sodium sulfate and evaporated down. Distillation gives 60 g of (B) of boiling point 175°–180° C./0.2 mbar.

Stage C

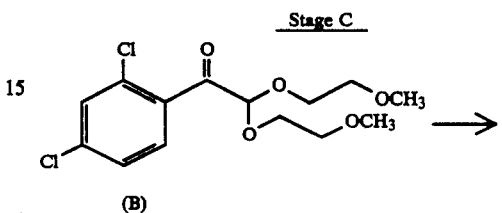

(B)

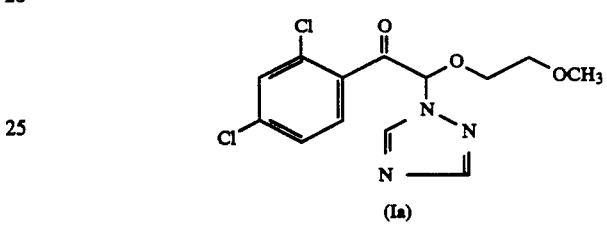

(Ia)

22 g of acetyl bromide are gradually added to 60 g of (B) at below 40° C. The resulting intermediate is added dropwise, without further purification, to a solution of 25 g of 1,2,4-triazole in 200 ml of tetrahydrofuran and 60 ml of dimethylformamide. The temperature should not exceed 30° C. during this procedure. The mixture is stirred for 13 hours at room temperature and filtered under suction, the filtrate is evaporated down, the residue is taken up with 500 ml of methylene chloride, and the solution is washed with water, dried over sodium sulfate and evaporated down.

98% strength nitric acid is added dropwise to the solution of the residue in ether, while cooling with ice. The resulting nitrate, which is an active ingredient of the formula Ia, is dried under reduced pressure to give 35 g of a compound of melting point 113° C. (This compound is listed as Example 18 in the table below.)

The nitrate is dissolved in methanol. The solution is rendered alkaline with aqueous ammonia and evaporated down, and the residue is taken up with methylene chloride. The solution is washed with water, dried over sodium sulfate and evaporated down. Distillation of the residue gives 20 g of an active ingredient of boiling point 183°–187° C./0.5 mbar, this active ingredient being listed as Example No. 17 in the table.

Stage D

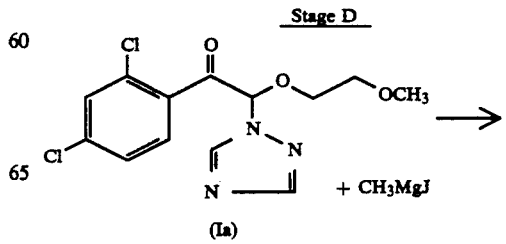

(Ia)

-continued
Stage D

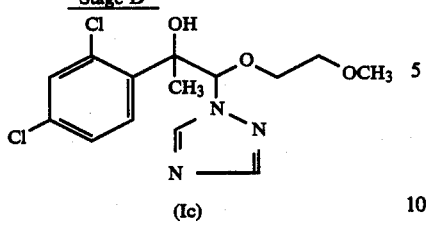
(Ic)

57 g of Ia in 200 ml of ether are added dropwise to a suspension of 0.35 mole of CH₃MgI in 500 mL of diethyl ether. The mixture is stirred under reflux for 2 hours, hydrolyzed with saturated aqueous ammonium chloride solution and extracted with diethyl ether. The extract is washed with aqueous sodium thiosulfate solution and water, dried over sodium sulfate and evaporated down to 200 ml. 98% strength nitric acid is added dropwise to the ice-cooled solution in ether. The nitrate precipitated during this procedure is recrystallized from ethyl acetate. 16 g of an active ingredient of melting point 133°–134° C. are obtained, this active ingredient being listed as Example No. 20 in the table.

The nitrate can be converted to the free base in the manner described (Example No. 21).

Stage E

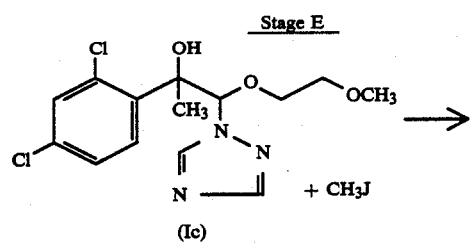 + CH₃J (Ic)

-continued
Stage E

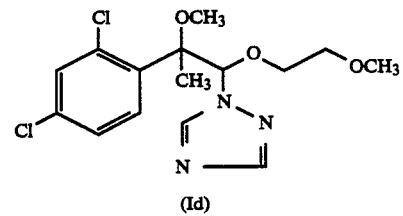
(Id)

3 g of sodium hydride, as an 80% strength suspension in paraffin, are added a little at a time to a solution of 29 g of (Ic) and 14.5 g of CH₃I in 390 ml of diethyl ether and 110 ml of dimethyl sulfoxide. When the evolution of hydrogen is complete, the mixture is refluxed for 30 minutes. 1.2 l of water are slowly added, and the mixture is again extracted with ether. The organic phase is washed with aqueous sodium thiosulfate solution and water, dried over sodium sulfate and evaporated down. Recrystallization of the crude product from diisopropyl ether gives 19 g of the active ingredient of melting point 122°–123° C., this active ingredient being listed as Example No. 24 in the table.

Other compounds according to the invention are listed in the table below; where physical properties are stated, the compounds have been prepared and their action investigated. The other compounds can be prepared by appropriately modifying the above instructions; because of their structural similarity, they are expected to have a similar action.

$$\text{(HX)}$$

structure with $(R^1)_n$ on phenyl, Z linker, O, $R^2$, $R^3$, $OR^4$, and triazole ring

| No. | $(R^1)_n$ | Z | $R^2$ | $R^3$ | $R^4$ | Mp. °C. (.HX) | Bp. °C./mbar |
|---|---|---|---|---|---|---|---|
| 1 | H | C=O | H | H | CH₃ | | |
| 2 | H | CHOH | H | H | CH₃ | | |
| 3 | H | CCH₃OH | H | H | CH₃ | | |
| 4 | H | CCH₃OH | H | H | C₆H₅ | | |
| 5 | 4-CH₃ | C=O | H | H | CH₃ | | |
| 6 | 4-CH₃ | CCH₃OH | H | H | CH₃ | | |
| 7 | 4-OCH₃ | C=O | H | H | CH₃ | | |
| 8 | 4-OCH₃ | CCH₃OH | H | H | CH₃ | | |
| 9 | 2-Cl | C=O | H | H | CH₃ | | |
| 10 | 2-Cl | CCH₃OH | H | H | CH₃ | | |
| 11 | 4-C₆H₅ | C=O | H | H | CH₃ | | |
| 12 | 4-C₆H₅ | CCH₃OH | H | H | CH₃ | | |
| 13 | 4-Cl | C=O | H | H | CH₃ | | |
| 14 | 4-Cl | CCH₃OH | H | H | CH₃ | | |
| 15 | 4-tBu | C=O | H | H | CH₃ | | |
| 16 | 4-tBu | CCH₃OH | H | H | CH₃ | | |
| 17 | 2,4-Cl₂ | C=O | H | H | CH₃ | | 183–7°/0.3 |
| 18 | 2,4-Cl₂ | C=O | H | H | CH₃ | 113° .HNO₃ | |
| 19 | 2,4-Cl₂ | CHOH | H | H | CH₃ | | |
| 20 | 2,4-Cl₂ | CCH₃OH | H | H | CH₃ | 133–4° .HNO₃ | |
| 21 | 2,4-Cl₂ | CCH₃OH | H | H | CH₃ | | |
| 22 | 2,4-Cl₂ | CCH=CH₂OH | H | H | CH₃ | | |
| 23 | 2,4-Cl₂ | CC₂H₅OH | H | H | CH₃ | | |

-continued

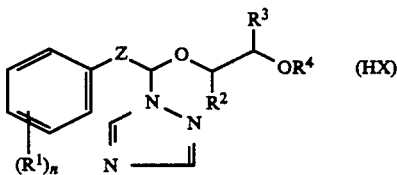
(HX)

| No. | $(R^1)_n$ | Z | $R^2$ | $R^3$ | $R^4$ | Mp. °C. (.HX) | Bp. °C./mbar |
|---|---|---|---|---|---|---|---|
| 24 | 2,4-$Cl_2$ | $CC_2H_5OH$ | H | H | $CH_3$ | 122–3° | |
| 25 | 2,4-$Cl_2$ | COCH$_2$CH=CH$_2$ \ CH$_3$ | H | H | $CH_3$ | | 170–4°/0.3 |
| 26 | 2,4-$Cl_2$ | COCH$_2$C$_6$H$_5$ \ CH$_3$ | H | H | $CH_3$ | | |
| 27 | 2,4-$Cl_2$ | C=O | H | $CH_3$ | $CH_3$ | | |
| 28 | 2,4-$Cl_2$ | $CCH_3OH$ | H | $CH_3$ | $CH_3$ | | |
| 29 | 2,4-$Cl_2$ | C=O | H | H | $C_2H_5$ | 101° .HNO$_3$ | |
| 30 | 2,4-$Cl_2$ | CHOH | H | H | $C_2H_5$ | | |
| 31 | 2,4-$Cl_2$ | $CCH_3OH$ | H | H | $C_2H_5$ | 148° .HNO$_3$ | |
| 32 | 2,4-$Cl_2$ | $CCH_3OH$ | H | H | $C_2H_5$ | 80° | |
| 33 | 2,4-$Cl_2$ | $CCH=CH_2OH$ | H | H | $C_2H_5$ | | |
| 34 | 2,4-$Cl_2$ | COCH$_2$CHCH$_2$ \ CH$_3$ | H | H | $C_2H_5$ | | |
| 35 | 2,4-$Cl_2$ | $CC_2H_5OH$ | H | H | $C_2H_5$ | | |
| 36 | 2,4-$Cl_2$ | $CCH_3OCH_3$ | H | H | $C_2H_5$ | | |
| 37 | 2,4-$Cl_2$ | $CCH_3OH$ | $CH_3$ | $CH_3$ | $CH_3$ | | |
| 38 | 2,4-$Cl_2$ | C=O | H | H | $C_6H_5$ | | |
| 39 | 2,4-$Cl_2$ | $CCH_3OH$ | H | H | $C_6H_5$ | | |
| 40 | 2,4-$Cl_2$ | C=O | H | H | iso-Propyl | | |
| 41 | 2,4-$Cl_2$ | $CCH_3OH$ | H | H | iso-Propyl | | |

EXAMPLES OF USE AS GROWTH REGULATORS

(A)

Vegetation trials were carried out on spring barley and field beans in Mitscherlich vessels. The plants were grown on a loamy sand which was adequately supplied with nutrients by means of a uniform basal dressing. The active ingredients were applied at defined plant heights, by spraying over the foliage. At the end of the trial, the height of growth of the plants was measured. The compound of Example 11 of German Laid-Open Application DOS 3,047,726 was chosen as a comparison.

It was found that the novel compound No. 31 has a superior growth-inhibiting action, ie. the test plants exhibited substantially more stunted growth coupled with a healthy appearance, the required application rate being lower than that in the case of the comparison.

(B)

To determine the growth-regulating property of the test substances, test plants were grown on a culture substrate adequately supplied with nutrients, in plastic vessels of about 12.5 cm diameter.

In the pre-emergence procedure, the test substances in aqueous formulation were poured onto the seed bed on the day of sowing. In the post-emergence procedure, the substances to be tested, in aqueous formulation, were sprayed onto the plants.

The growth-regulating action observed was confirmed at the end of the trial by measuring the height of growth. The measured values thus obtained were expressed as a ratio of the height of growth of the untreated plants. The same substance as in the trial above was used as a comparative substance.

In these trials, which were carried out on spring wheat, spring barley, rice, sunflowers, summer rape, soybean, etc., it was found that, for example, the active ingredients 20, 21, 29 and 31 exhibited a particularly advantageous action on the growth in height.

Simultaneously with the reduction in the growth in height, the color intensity of the leaves increased. Because of the increase of chlorophyl content the photosynthesis rate and hence the yield are also expected to be higher.

EXAMPLES OF USE AS FUNGICIDES

(C)

Effectiveness against powdery mildew of wheat; preventive spraying

Leaves of wheat seedlings of the Frühgold variety grown in pots were sprayed with an aqueous spray liquor obtained by diluting a concentrate containing 80% of active ingredient and 20% of emulsifier and, 24 hours after the spray coating had dried, dusted with oidia (spores) of powdery mildew of wheat (*Erysiphe graminis* var. tritici). The test plants were then placed in a greenhouse at from 20° to 22° C. and from 75 to 80% relative humidity. After 7 days, the extent of powdery mildew development was determined. Evaluation as effected by rating the fungal infestation on a scale from 0 to 5 and the leaf damage with A, B, C or T (total damage). In this trial, the active ingredients 18, 20, 21, 24, 31 and 32 achieved virtually complete inhibition of infestation throughout with only 0.06% strength spray liquor, whereas the untreated comparison exhibited total infestation.

(D)

Effectiveness against powdery mildew of cucumber; treatment after spore action

Leaves of cucumber seedlings of the Chinesische Schlange variety grown in pots were sprayed, at the two-leaf stage, with a spore suspension of powdery mildew of cucumber. After about 20 hours, the test plants were sprayed with an aqueous spray liquor obtained by diluting a concentrate containing 80% of active ingredient and 20% of emulsifier, spraying being continued until the plants were dripping wet. After the spray coating had dried on, the plants were placed in a greenhouse at from 20° to 22° C. and from 70 to 80% relative humidity. To assess the effectiveness of the novel substances, the extent of fungal development was determined after 21 days.

In this trial, in which once again infestation was rated on a scale from 0 to 5, a concentration of 0.025% of the active ingredients 18, 20, 31 and 32 prevented the occurrence of damage symptoms in virtually every case, whereas the untreated comparison exhibited total infestation.

(E)

Effectiveness against brown rust of wheat; treatment after infection

Leaves of wheat seedlings of the Frühgold variety grown in pots were dusted with spores of brown rust (Puccinia recondita). Thereafter, the pots were placed in a chamber at from 20° to 22° C. and high relative humidity (90–95%) for 24 hours. During this time, the spores germinated and the germ tubes penetrated the leaf tissue. Where no treatment with fungicides was carried out, this led to loss of the plant; the infection was confirmed by means of a control trial.

The infected plants were then sprayed, until dripping wet, with an aqueous spray liquor obtained by diluting a concentrate-containing 80% of active ingredient and 20% of emulsifier. After the spray coating had dried on, the test plants were placed in a greenhouse at from 20° to 22° C. and from 65 to 70% relative humidity. After 8 days, the extent of development of rust fungi on the leaves was determined.

Evaluation was carried out as described above. It was found that active compounds No. 20, 21, 24, 31 and 32 substantially prevent visible infestation at a concentration of only 0.006% in the spray liquor, while virtually complete protection is achieved when the concentration used is 0.025%.

(F)

Effectiveness against *Pyrenophora teres*; preventive treatment

Barley seedlings of the Asse variety were sprayed at the two-leaf stage with aqueous suspensions containing 80% of active ingredient and 20% of emulsifier in the dry substance, spraying being continued until the seedlings were dripping wet. After 24 hours, the plants were inoculated with a spore suspension of the fungus *Pyrenophora teres* and were placed for 48 hours in a conditioned chamber having a high atmospheric humidity and at 18° C. Thereafter, the plants were cultivated in a greenhouse at 20°–22° C. and 70% relative humidity for another 5 days. The extent of development of the symptoms was then determined, and evaluated as described above.

In these trials, compounds 20, 21 and 31 exhibited a good or excellent action even in 0.05% strength formulation, whereas the untreated crops were lost.

As shown by the above trials, the novel compounds also possess excellent activity against a broad spectrum of phytopathogenic fungi, in particular those from the class consisting of the Ascomycetes and Basidiomycetes. Some of these compounds possess systemic activity and can be used as foliar and soil fungicides.

The fungicidal compounds are of particular interest for controlling a large number of fungi on various crops or their seed, in particular wheat, rye, barley, oats, rice, corn, cotton, soybean, coffee, sugar cane, fruit and ornamentals in horticulture, in viticulture and for vegetables, such as cucumbers, beans and cucurbits.

The novel compounds are suitable, for example, for controlling the following plant diseases:
*Erysiphe graminis* (powdery mildew) in cereals,
*Erysiphe cichoracearum* on cucurbits,
*Podosphaera Leucotricha* on apples,
*Uncinula necator* on grape vines,
Puccinia species on cereals,
*Rhizoctonia solani* on cotton,
Ustilago species on cereals and sugar cane,
*Venturia inaequalis* (scab) on apples,
*Septoria nodorum* on wheat,
*Botrytis cinerea* (gray mold) on strawberries and grape vines,
*Cercospora arachidicola* on peanuts,
*Pseudocercosporella herpotrichoides* on wheat and barley,
*Pyricularia oryzae* on rice,
*Hemileia vastatrix* on coffee,
*Alternaria solani* on potatoes and tomatoes,
*Plasmopara viticola* on grape vines and
Fusarium and Verticillium species on various plants.

ACTION OF THE NOVEL SUBSTANCES AS GROWTH REGULATORS

EXAMPLE 1

Greenhouse trials

To determine the growth-regulating properties of the active ingredients, test plants were grown on a culture substrate adequately supplied with nutrients, in plastic vessels of about 12.5 cm diameter.

In the pre-emergence procedure, the active ingredients in aqueous formulation were poured onto the seed bed on the day of sowing.

In the post-emergence procedure, the active ingredients in aqueous formulation were sprayed onto the plants. The growth-regulating action observed was confirmed at the end of the trial by measuring the height of growth. The measured values thus obtained were expressed as a ratio of the height of growth of the untreated plants. The active ingredient of Example 11 of US-A-4 436 548 (A) was used as a comparative substance.

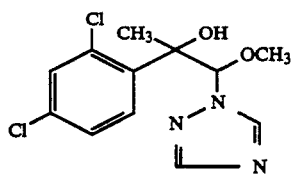

(A)

Simultaneously with the reduction in the growth in height, the color intensity of the leaves increased. Because of the increased chlorophyll content, the photosynthesis rate and hence the yield are also expected to be higher.

The specific data are given in the tables below.

TABLE 1

Spring wheat, Kolibri variety
Post-emergence foliage treatment

| No. of chemical example | Concentration, mg of ai/vessel | Relative heights of growth |
|---|---|---|
| Untreated | — | 100 |
| A | 6 | 93.7 |
| 20 | 6 | 88.5 |
| 21 | 6 | 87.7 |
| 31 | 6 | 82.3 |
| 32 | 6 | 85.9 |

TABLE 2

Spring barley, Aramir variety
Post-emergence foliage treatment

| No. of chemical example | Concentration, mg of ai/vessel | Relative heights of growth |
|---|---|---|
| Untreated | — | 100 |
| A | 6 | 94.0 |
| 20 | 6 | 93.6 |
| 21 | 6 | 86.4 |
| 31 | 6 | 75.3 |
| 32 | 6 | 89.1 |

TABLE 3

Rice, Nihonbare variety
Post-emergence soil treatment

| No. of chemical example | Concentration, mg of ai/vessel | Relative heights of growth |
|---|---|---|
| Untreated | — | 100 |
| A | 1.5 | 99.8 |
|  | 6 | 99.8 |
| 20 | 1.5 | 98.8 |
|  | 6 | 88.9 |
| 31 | 1.5 | 93.8 |
|  | 6 | 82.3 |
| 32 | 1.5 | 91.2 |
|  | 6 | 84.3 |

TABLE 4

Sunflowers, Sorex variety
Post-emergence foliage treatment

| No. of chemical example | Concentration, mg of ai/vessel | Relative heights of growth |
|---|---|---|
| Untreated | — | 100 |
| A | 6 | 96.8 |
| 20 | 6 | 90.2 |
| 21 | 6 | 84.4 |
| 29 | 6 | 79.5 |
| 31 | 6 | 78.4 |

TABLE 5

Summer rape, Petranova
Post-emergence foliage treatment

| No. of chemical example | Concentration, mg of ai/vessel | Relative heights of growth |
|---|---|---|
| Untreated | — | 100 |
| A | 6 | 92.4 |
| 20 | 6 | 85.0 |
| 21 | 6 | 69.4 |
| 29 | 6 | 79.6 |
| 31 | 6 | 72.6 |
| 32 | 6 | 68.8 |

TABLE 6

Soybean, Maple Arrow
Post-emergence foliage treatment

| No. of chemical example | Concentration, mg of ai/vessel | Relative heights of growth |
|---|---|---|
| Untreated | — | 100 |
| A | 0.5 | 92.5 |
|  | 1.5 | 92.5 |
| 20 | 0.5 | 91.7 |
|  | 1.5 | 86.2 |
| 31 | 0.5 | 84.4 |
|  | 1.5 | 73.4 |

EXAMPLE 2

Vegetation trials

Vegetation trials were carried out on spring barley and field beans in Mitscherlich vessels. The plants were grown on a loamy sand which was adequately supplied with nutrients by means of a uniform basal dressing. The active ingredients were applied at defined plant heights, by spraying over the foliage. At the end of the trial, the height of growth of the plants was measured. The prior art substance BAS 110 00 W (Example 11 from German Laid-Open Application DOS 3,047,726) was used as a comparative substance.

It was possible to show that the novel compound 192 242 (No. 31) had a superior growth-inhibiting action.

| No. of chemical example | Application rate, mg/vessel | Height of growth, cm |
|---|---|---|
| Vegetation trial for spring barley | | |
| Untreated | — | 61.0 |
| A | 10 | 57.5 |
|  | 20 | 52.0 |
| 31 | 10 | 54.8 |
|  | 20 | 51.0 |
| Vegetation trial for field beans | | |
| Untreated | — | 83.3 |
| A | 5 | 81.0 |
|  | 10 | 80.0 |
| *31 | 5 | 73.5 |
|  | 10 | 70.0 |

We claim:
1. An α-triazolyl glycol ether of the formula I

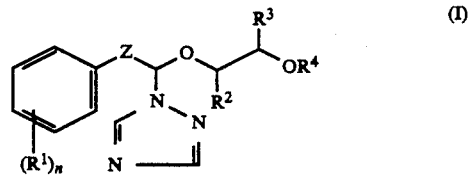

where
$R^1$ is $C_1$–$C_4$-alkyl, $C_1$–$C_4$-alkoxy, halogen or phenyl, $R^2$ and $R^3$ are each hydrogen or $C_1$–$C_4$-alkyl, $R^4$ is $C_1$–$C_4$-alkyl Z is

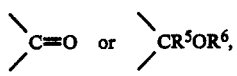

n is 0, 1, 2 or 3

$R^5$ is hydrogen, $C_1$–$C_4$-alkyl, vinyl, allyl, prop-1-en-1-yl ethynyl, prop-1-yn-1-yl, but-1-yn-1-yl and $R^6$ is hydrogen, $C_1$–$C_4$-alkyl, allyl, crotyl, benzyl, halogenbenzyl, 4-methylbenzyl, 4tert-butylbenzyl, 4-methoxybenzyl, 2-methoxybenzyl or 4-isopropoxybenzyl.

2. The α-triazolyl glycol ether of claim 1, wherein $(R^1)_n$ is 2,4-$Cl_2$, $R^2$ and $R^3$ are each hydrogen, $R^4$ is ethyl and Z is $CR^5OR^6$ in which $R^5$ is methyl and $R^6$ is hydrogen.

3. A plant growth regulator composition for reducing the growth height of plants comprising a carrier and an effective amount of a triazolyl glycol ether as defined in claim 1 as the active ingredient.

4. A method of controlling fungi comprising applying a fungicidally effective amount of a triazolyl glycol ether as defined in claim 1 to plants, seed or soil threatened with fungal attack.

5. A method for reducing the growth height of plants comprising applying an effective amount of a triazolyl glycol ether as defined in claim 1 to plants or their seed.

* * * * *